US012645913B2

(12) United States Patent (10) Patent No.: US 12,645,913 B2

Gladden (45) Date of Patent: Jun. 2, 2026

(54) APPARATUS FOR ENHANCING LONGEVITY AND A METHOD FOR ITS USE

(71) Applicant: Oceandrive Ventures, LLC, New York, NY (US)

(72) Inventor: Jeffrey Gladden, Rio Grande, PR (US)

(73) Assignee: Oceandrive Ventures, LLC, Rio Grande, PR (US)

( * ) Notice: Subject to any disclaimer, the term of this patent is extended or adjusted under 35 U.S.C. 154(b) by 0 days.

(21) Appl. No.: 17/952,620

(22) Filed: Sep. 26, 2022

(65) Prior Publication Data

US 2024/0104340 A1 Mar. 28, 2024

(51) Int. Cl.
| | |
|---|---|
| *G06N 3/08* | (2023.01) |
| *G06N 3/04* | (2023.01) |
| *G16H 20/30* | (2018.01) |

(52) U.S. Cl.
CPC ................. *G06N 3/04* (2013.01); *G06N 3/08* (2013.01); *G16H 20/30* (2018.01)

(58) Field of Classification Search
CPC ............. G06N 3/04; G06N 3/08; G16H 20/30
See application file for complete search history.

(56) References Cited

U.S. PATENT DOCUMENTS

| | | | |
|---|---|---|---|
| 11,227,691 B2 | 1/2022 | Neumann et al. | |
| 2017/0290516 A1 | 10/2017 | Nguyen | |

| | | | |
|---|---|---|---|
| 2018/0150609 A1* | 5/2018 | Kim | G06N 3/04 |
| 2020/0380887 A1 | 12/2020 | Mason | |
| 2021/0166137 A1* | 6/2021 | Neumann | G06N 5/04 |

FOREIGN PATENT DOCUMENTS

| | | |
|---|---|---|
| CN | 113539487 | 4/2020 |
| KR | 101488592 B1 | 1/2015 |

OTHER PUBLICATIONS

George-Gay, B., et al, Understanding the Complete Blood Count With Differential, Retrieved from Internet:<https://www.sciencedirect.com/science/article/pii/S1089947203000042> (Year: 2003).*

(Continued)

*Primary Examiner* — Miranda M Huang
*Assistant Examiner* — Bart I Rylander
(74) *Attorney, Agent, or Firm* — Caldwell LLC

(57) ABSTRACT

An apparatus for enhancing longevity, wherein the apparatus includes at least a processor and a memory communicatively connected to the processor, the memory containing instructions configuring the at least a processor to receive a longevity measurement related to a user and calculate a longevity parameter as a function of the longevity measurement. The memory containing instructions further configuring the processor to assign the user a longevity level, including training a longevity classifier using a longevity training data containing a plurality of data entries correlating examples of longevity parameters to examples of longevity levels, classifying the longevity parameter to the longevity level using the longevity classifier, and assigning the user the longevity level as a function of the classification. The memory containing instructions further configuring the processor to generate a longevity plan as a function of the longevity parameter and longevity level.

18 Claims, 9 Drawing Sheets

200

(56) References Cited

OTHER PUBLICATIONS

Bellavia, A., et al, Using Laplace Regression to Model and Predict Percentiles of Age at Death When Age is the Primary Time Scale , Retrieved from Internet:<https://academic.oup.com/aje/article/182/3/271/167476> (Year: 2015).*

Nedungadi, P, et al, Personalized Health Monitoring System for Managing Well-Being in Rural Areas, Retrieved from Internet:<https://link.springer.com/article/10.1007/s 10916-017-0854-9> (Year: 2018).*

Xia, X., et al, Assessing the rate of aging to monitor aging itself, Retrieved from Internet:<https://www.sciencedirect.com/science/article/pii/S1568163721000970> (Year: 2021).*

Foreman, A., et al, Age estimation from sleep studies using deep learning predicts life expectancy, Retrieved from Internet:<https://www.nature.com/articles/s41746-022-00630-9> (Year: 2022).*

Sivaram, M., et al, Advanced Expert System Using Particle Swarm Optimization Based Adaptive Network Based Fuzzy Inference System to Diagnose the Physical Constitution of Human Body, Retrieved from internet:<https://link.springer.com/chapter/10.1007/978-981-13-8300-7_29> (Year: 2019).*

Dorresteijn, J. et al, How to translate clinical trial results into gain in healthy life expectancy for individual patients, Retrieved from Internet:<https://www.bmj.com/content/352/bmj.i1548.abstract> (Year: 2016).*

Foreman, K., et al, Forecasting life expectancy, years of life lost, and all-cause and cause-specific mortality for 250 causes of death . . ., Retrieved from Internet:<https://www.sciencedirect.com/science/article/pii/S0140673618316945> (Year: 2018).*

Faisal, K., et al, Life Expectancy Estimation based on Machine Learning and Structured Predictors, Retrieved from Internet:<https://dl.acm.org/doi/fullHtml/10.1145/3503047.3503122> (Year: 2021).*

Sansrimahachai, W., Personalized Walking Exercise Support System for Elderly Based on Machine Learning, Retrieved from Internet:<https://ieeexplore.ieee.org/abstract/document/9268327> (Year: 2020).*

Zhang, Y., et al, How to Retrain Recommender System? A Sequential Meta-Learning Method, Retrieved from Internet:<https://dl.acm.org/doi/abs/10.1145/3397271.3401167> (Year: 2020).*

* cited by examiner

Longevity Database 300

Longevity Measurement 108

Longevity Parameter 112

Longevity Level 116

Longevity Plan 120

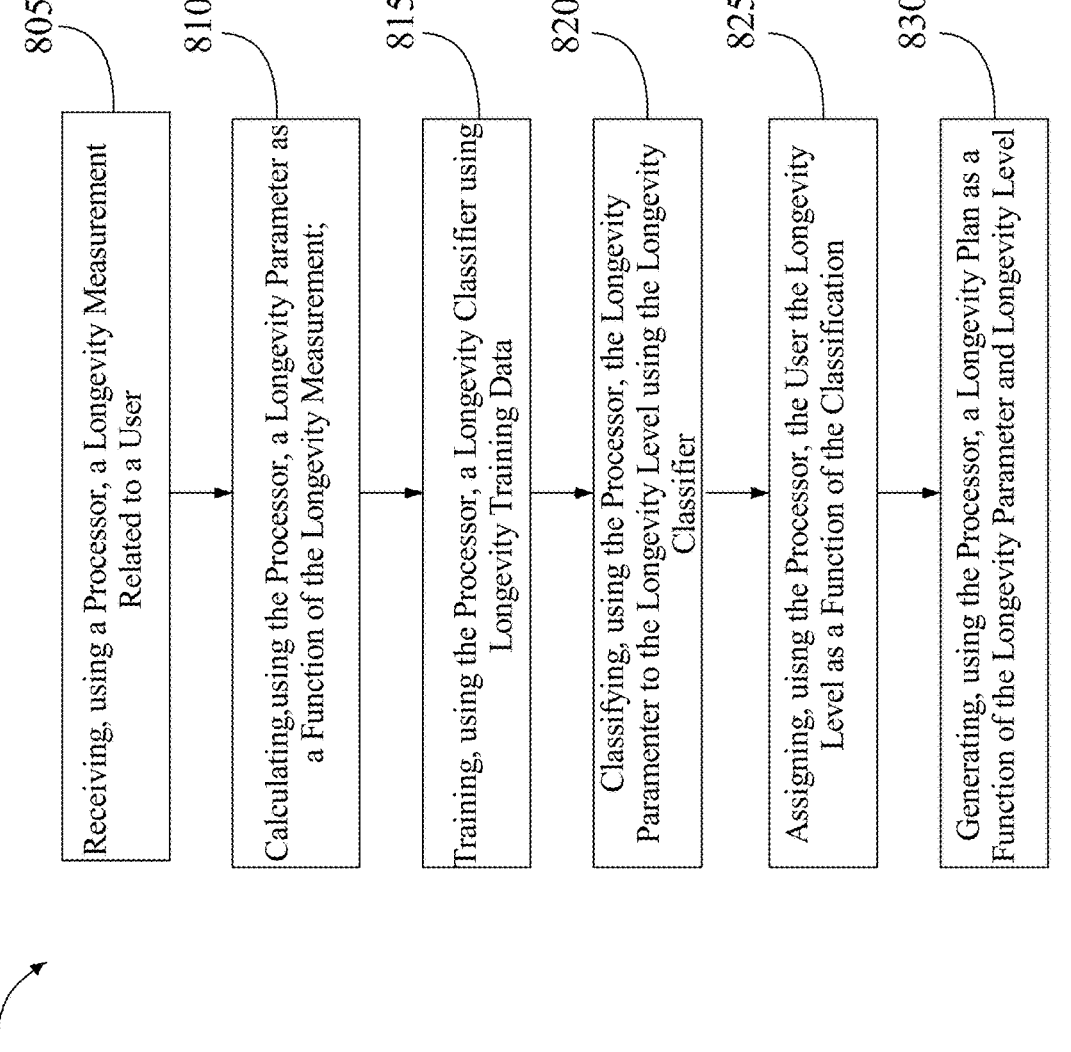

805 — Receiving, using a Processor, a Longevity Measurement Related to a User

810 — Calculating, using the Processor, a Longevity Parameter as a Function of the Longevity Measurement;

815 — Training, using the Processor, a Longevity Classifier using Longevity Training Data 820 — Classifying, using the Processor, the Longevity Parameter to the Longevity Level using the Longevity Classifier 825 — Assigning, uisng the Processor, the User the Longevity Level as a Function of the Classification 830 — Generating, using the Processor, a Longevity Plan as a Function of the Longevity Parameter and Longevity Level

APPARATUS FOR ENHANCING LONGEVITY AND A METHOD FOR ITS USE

FIELD OF THE INVENTION

The present invention generally relates to the field of health technologies. In particular, the present invention is directed to an apparatus for enhancing longevity and a method for its use.

BACKGROUND

Increasing human longevity is a complex, multifaceted problem. Depending on particular health status and issues of patients, a tailored plan may be necessary to improve the longevity of a patient. Existing solutions to this problem are not satisfactory.

SUMMARY OF THE DISCLOSURE

In an aspect, an apparatus for enhancing longevity, wherein the apparatus includes at least a processor and a memory communicatively connected to the processor, the memory containing instructions configuring the at least a processor to receive a longevity measurement related to a user and calculate a longevity parameter as a function of the longevity measurement. The memory containing instructions further configuring the processor to assign the user a longevity level as a function of the longevity parameter, wherein assigning includes training a longevity classifier using a longevity training data, wherein the longevity training data contains a plurality of data entries correlating examples of longevity parameters to examples of longevity levels, classifying the longevity parameter to the longevity level using the longevity classifier, and assigning the user the longevity level as a function of the classification. The memory containing instructions further configuring the processor to generate a longevity plan as a function of the longevity parameter and longevity level.

In another aspect, a method for enhancing longevity is shown, the method includes receiving, using a processor, a longevity measurement related to a user. The processor calculates longevity parameter as a function of the longevity measurement. Additionally, the processor trains longevity classifier using a longevity training data wherein the longevity training data contains a plurality of data entries correlating a examples of longevity parameter to examples of longevity level. The longevity parameter is classified to the longevity level using the longevity classifier. The processor assigns the user a longevity level as a function of the classification. A longevity plan is be generated as a function of the longevity parameter and longevity level.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 8 is a flow diagram of an exemplary method of enhancing longevity; and

The drawings are not necessarily to scale and may be illustrated by phantom lines, diagrammatic representations, and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for enhancing longevity. The apparatus may comprise at least a processor and a memory communicatively connected to the processor. The processor may further be configured to receive a longevity measurement related to a user. The processor then may calculate a longevity parameter as a function of the longevity measurement. The users is them assigned a longevity level as a function of the longevity parameter. Assigning a longevity level further includes training a longevity classifier using a longevity training data wherein the longevity training data contains a plurality of data entries correlating a longevity parameter to a longevity level. The longevity parameter may then be classified to the longevity level using the longevity classifier. The user is then assigned a longevity level as a function of the classification. The processor then may generate a longevity plan as a function of the longevity parameter and longevity level. Exemplary embodiments illustrating aspects of the present disclosure are described below in the context of several specific examples.

Figure 1:
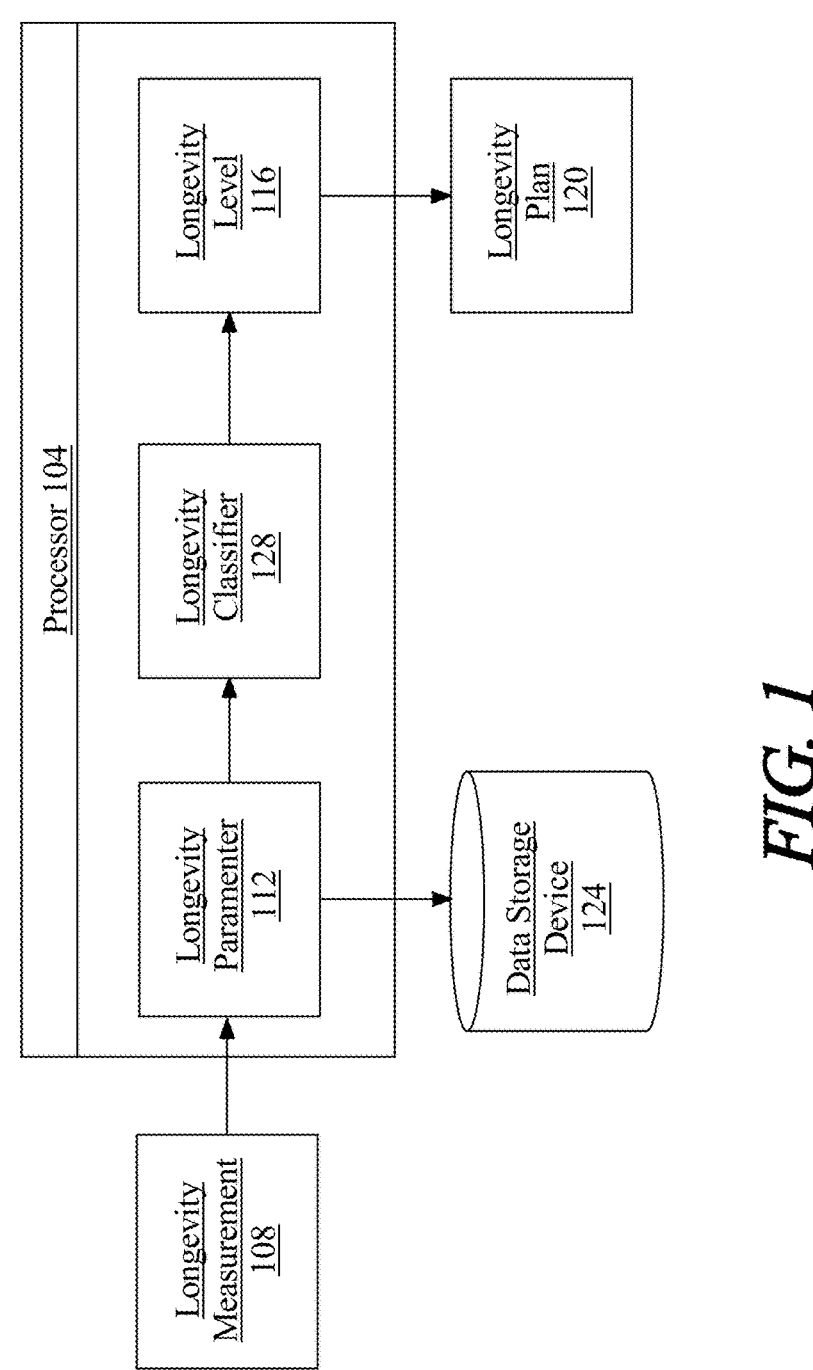
FIG. 1 is a block diagram of an exemplary embodiment of an apparatus for enhancing longevity.

Referring now to FIG. 1, an exemplary embodiment of an apparatus 100 for enhancing longevity and a method for its use is illustrated. System includes a Processor 104. Processor 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Processor 104 may include a single computing device operating independently, or may include two or more computing device operating in concert, in parallel, sequentially or the like; two or more computing devices may be included together in a single computing device or in two or more computing devices. Processor 104 may interface or communicate with one or more additional devices as described below in further detail via a network interface device. Network interface device may be utilized for connecting Processor 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Processor 104 may include but is not limited to, for example, a computing device or cluster of computing devices in a first location and a second computing device or cluster of computing devices in a second location. Processor 104 may include one or more computing devices dedicated to data storage, security, distribution of traffic for load balancing, and the like. Processor 104 may distribute one or more computing tasks as described below across a plurality of computing devices of computing device, which may operate in parallel, in series, redundantly, or in any other manner used for distribution of tasks or memory between computing devices. Processor 104 may be implemented using a "shared nothing" architecture in which data is cached at the worker, in an embodiment, this may enable scalability of apparatus 100 and/or computing device.

With continued reference to FIG. 1, processor 104 may be designed and/or configured to perform any method, method step, or sequence of method steps in any embodiment described in this disclosure, in any order and with any degree of repetition. For instance, Processor 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Processor 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Continuing in reference to FIG. 1, processor 104 may receive, from a user, longevity measurement 108. In some embodiments, longevity measurement 108 may be stored in a database, such as longevity database 300 disclosed with reference to FIG. 3. As used in this disclosure, "receive" from a user means accepting, collecting, or otherwise receiving input from a user and/or device. A "longevity measurement," as used in this disclosure, is data that relates to the user's systems, life energy, longevity age, health age, or performance metrics. In some embodiments, the longevity measurement may be calculated as function of longevity data. In other embodiments, the longevity measurement may relate to the age of a user's systems. Longevity measurement 108 may take into account chemical, biological, physical, and behavioral data relating to a user. Additionally, a longevity measurement 108 may also evaluate a user's age as it relates to their natural, social, and built environments. In non-limiting illustrative examples, a longevity measurement 108 may be a combination of a user's health data including medical history, user diet, exercise, sleep, data corresponding to timestamps and geographical locations for how a user spends his or her time, data regarding how a user spends money, user social media information, and the like. In other embodiments, a longevity measurement 108 may include information collected from a standard health screening such as electrolyte level, kidney function, blood count, hydration status, and the like. A health screening may include tests like Complete Blood Count, Prothrombin Time. Basic Metabolic Panel, Comprehensive Metabolic Panel, Lipid Panel. Liver Panel, Thyroid Stimulating Hormone, Hemoglobin A1C. The health measurement may include more comprehensive analysis such as results from a screening test or diagnostic medical procedure.

With continued reference to FIG. 1, Longevity measurement 108 may include data relating to user's performance metrics. As used in the current disclosures, a "performance metric" is the ability of the user to perform a predetermined task or set of tasks. User abilities that may be tested in a performance metric may include the users speed, flow state, agility, resilience, strength, grip strength, core strength, quickness, static balance, dynamic balance, recovery, flexibility, cardiovascular endurance, neuromuscular reaction time, and the like.

With continued reference to FIG. 1, Longevity measurement 108 may include data relating to user's longevity age. As used in the current disclosure, a "longevity age" is an element of data relating to the users age in terms of the users microbiology. In a non-limiting example, a user's longevity age may be evaluated in terms of the user's telomeres, mitochondria, proteomic, glycans, oncogenic, epigenetic rate of aging, epigenetic urine, DNA repair, epigenetic intrinsic, epigenetic extrinsic, mTOR AMPK balance, NAD, NADH, Stem Cells, Senescent Cell Burden, Senescent cell SASP, Immune system, and Inflammation. As used in the current disclosure, "life energy" is an evaluation of the status users metal health. This may include an evaluation of a user's mental health regarding overall energy, safety, wisdom, spiritual health, overall joy, relationship health, growth mindset, and overall mental health. In an embodiment, an evaluation of a user's life energy may encompass an evaluation from a mental health professional and/or user inputs.

With continued reference to FIG. 1, Longevity measurement 108 may include data relating to user's health age. As used in the current disclosure, a "health age" is the age of the user in term of overall user health. In a non-limiting example, a user's health age may be evaluated in terms of gut biome health, digestive system health, esophagus health, stomach health, thyroid health, metabolic health, insulin levels, sugar intake, pancreatic health, live health, kidney health, HPA Axis, Auditory system health, Tinnitus, Visual activity, Presbyopia, cataracts, glaucoma retinal issues, AMD, Cancer Risk, Body Composition, Hair health, Skin health, Nails, Sleep quality, Heart VO2 MAX, Vascular anatomic health, vascular functional health, lung health, sex hormones levels, blood, urine, saliva, sexual function, brain function, brain anatomic, Peripheral NS, Bone health, Joint health, Ligament health, Tendon health, Muscle health, and the like.

With continued reference to FIG. 1, Longevity measurement 108 may include data relating to user's systems. As used in the current disclosure, "systems" are a human's biological systems. A user's systems may include but is not limited to the circulatory, nervous, skeletal, respiratory, reproductive, endocrine, integumentary, renal, digestive, and muscular systems. Each organ may have one or more specialized role in the body and is made up of distinct tissues. Additionally, a user's systems may include the heart, lungs, kidneys, or any other organ system. This may also include the components of a given system. In a non-limiting example, the lungs may be component of the respiratory system.

With continued reference to FIG. 1, Longevity measurement 108 may include measure able biomarkers. As used in the current disclosure, a "biomarker" is a biological molecule found in blood, other body fluids, or tissues that is a sign of a normal or abnormal process, or of a condition or disease. A biomarker may be used to see how well the body responds to a treatment for a disease or condition. A measurable biomarker may include but is not limited to, yH2A.X immunohistochemistry, Leukocyte telomere length, MIR31HG, p16INK4a, Senescence-associated secretory phenotype (SASP) proteins, Measures of DNA methylation, SIRT1, SIRT2, SIRT3, SIRT6, SIRT7, Dosage of circulating microRNAs (miR-34a, MiR-21, miR-126-3p, miR-151a-3p, miR-181a-5p, miR-1248), P31 MRI spectroscopy, growth differentiating factor 15 (GDF15), Target of rapamycin (TOR), Protein carbonylation, Advanced glycation end products, Insulin-like growth factor (IGF-1), HGBA1c, IL-6, TNF-α, CRP (C-reactive protein), and TNFRII (tumor necrosis factor-α RII). These biomarkers may be measured using various pathways including, but not limited to, DNA repair mechanisms, DNA modifications, telomere length, markers of DNA damage response, telomerase activity, senescent markers in blood and tissue, DNA methylation, histone acetylation, noncoding RNA, autophagy markers, chaperon proteins, proliferative capacity in vitro, growth hormone axis, and metabolism alterations.

With continued reference to FIG. 1, processor 104 may be configured to identify longevity data related to a particular user. A "longevity data," as used in this disclosure, contains at least an element of data related to the user's anatomy data as it relates to age. As used in this disclosure, "anatomy data" is any data indicative of a user's physical health as it relates to age. A user's physical health may include the health of various user systems including the user's circulatory system, a digestive system, a nervous system, reproductive system, endocrine system, skeletal system, and/or the like. This may additionally include one or more organs within each system within a user's body. Additionally, anatomy data may include various information about the users cell, tissues, bodily fluid, and the like. A user's anatomy data may be gathered by using a plurality of plurality of tests. As used in the current disclosures, "tests" refers to any medical test used to extract information about a user's systems. Tests may include various blood, imaging, functionality, lab tests, sleep tests, psychological evaluations, blood tests, urine tests, stool samples, evaluations by a medical professional, and the like. Examples of tests may include various blood tests like complete blood count test, a basic metabolic panel, a blood enzyme test, cholesterol tests, triglyceride tests, blood clotting tests, blood glucose test, blood oxygen test, and the like. Additional tests may be used to generate anatomy data may include various imaging tests such as an MRI, Xray, Mammogram, ultrasound, fluoroscopy, pet scans, and the like. A person who is reasonably skilled in the art, after having reviewed the entirety of this disclosure, would appreciate that various types of tests may be used determine the age, health, or status of the user's system.

With continued reference to FIG. 1, a processor 104 may receive longevity measurement 108 from wearable device data that tracks how a user relates with his or her environments. As used in the current disclosure, a "wearable device" is a computing device that is designed to be worn on a user's body or clothing. The wearable device may detect wearable device data. In embodiments, a wearable device may include a smart watch, smart ring, fitness tracking device, and the like. As used in the current disclosure, "wearable device data" is data collected by a wearable device. Wearable device data may include data and associated analysis corresponding to, for instance and without limitation, accelerometer data, pedometer data, gyroscope data, electrocardiography (ECG) data, electrooculography (EOG) data, bioimpedance data, blood pressure and heart rate monitoring, oxygenation data, biosensors, fitness trackers, force monitors, motion sensors, video and voice capture data, social media platform data, and the like. Longevity measurement 108 may be provided by a user or a second individual on behalf of a user, for instance and without limitation a physician, medical professional, nurse, hospice care worker, mental health professional, and the like. Longevity measurement 108 may originate from a user questionnaire, graphical user interface (GUI), or any other suitable forum for gathering information regarding longevity data. Persons skilled in the art, upon review of this disclosure in its entirety, will be aware of the various ways in which longevity data may be collected and provided to the system described herein.

With continued reference to FIG. 1, a processor 104 may calculate a longevity parameter 112 as a function of a longevity measurement 108. As used in the current disclosure, a "longevity parameter" is an element of data that indicates the age of a user's systems. Longevity parameter 112 may be calculated as the difference between the users the users age comparison metric and actual age. In embodiments, a longevity parameter that is 0 reflects an average user for their given age. This user's systems maybe aging at an appropriate rate. If a longevity parameter is a negative number, the user's systems may be aging faster than their actual age. This may mean that the user's system is unhealthy. The larger the negative number the more severe the aging is for a given user. A longevity parameter may indicate the age of a user's system in relation to their actual age. In a non-limiting example, a Longevity parameter 112 may indicate immune system age, telomere age, metabolic age, mitochondrial age, hormone age, transcriptomic age, performance age, and the like. The longevity parameter may include an indication of timing of aging, sequence of aging, frequency of aging, intensity of aging, and the like. A longevity parameter may be calculated using an age comparison metric. As used in the current disclosure, an "age comparison metric" is a comparison of the current state of a system compared to the average system of a person of a similar age. Age comparison metric may also take into account a person's gender, weight, substance abuse, family health history, life energy, overall health, performance metrics, and the like. An age comparison metric may take into account the lifestyle choices of a user. For example, an age comparison metric may compare a 30-year-old male user who drinks alcohol to the average health of a 30-year-old male who drinks alcohol. An age comparison metric may also compare the 30-year-old male who drinks alcohol to all 30-year-old male users. In another non-limiting example, an age comparison metric may compare the performance metrics for a 35-year-old female to the performance metrics of all 35-year-old female users. The longevity parameter may be calculated using a machine learning model or fuzzy sets. A user's "actual age," as defined in this disclosure, is the length of time since a person's birth in years.

With continued reference to FIG. 1, The age comparison metric may include a calculation of the rate of aging. As used in the current disclosure, a "rate of aging" is an indication of the rate of change of age as a function of health of a given system. In embodiments, the rate of aging may take into account the systems life energy, overall health, and performance metrics. Rate of aging may be used to determine how quickly a given system is aging. Rate of aging may also apply to a given component of a system. Rate of aging may be reflected in terms of a ratio or a fraction. The difference between a first and a second longevity parameter 112 a numerator and the time between evaluations as denominator. Wherein the first longevity parameter (LP1) is taken at the first evaluation and the second longevity parameter (LP2) is taken at the second evaluation.

$$\text{Rate of Aging} = \frac{LP1 - LP2}{\text{Time between evaluations}}$$

For example, a 25-year-old user may have a liver health similar to a 35-year-old on the first evaluation, thus he may have a longevity parameter of 10. During the second evaluation, approximately 1 year later, the 25-year-old user may have a liver health similar to a 45-year-old thus he may have a longevity parameter of 20. The rate of aging of the 25-year-old user will be approximately −10. This may mean that the user's system is aging at 10× the rate of a normal person. In reference to the rate of aging a score ranging from −1 to 1 may be considered normal. In an embodiment, the further the rate of aging is away from 0 the faster the user is aging either positively or negatively. Positive ageing is when the system is getting progressively healthier and thus comparable to a younger person. Negative aging is when the system is getting progressively older and thus comparable to an older person. When the rate of aging is a negative number the user's systems may be getting growing older at a faster rate than normal. When the rate of aging is positive the user's system may be getting younger, and thus progressively healthier.

Still referring to FIG. 1, a "average longevity parameter," as used in this disclosure is a singular numerical value that summarizes a plurality of longevity parameter 112. The average longevity parameter may include a numerical value relates to the age of some or all a user's systems as a function of their health. In non-limiting illustrative examples, an average longevity parameter may be a numerical value that summarizes a user's age as it relates to current nutrition, substance abuse, sleep deprivation, exercise frequency, body mass index (BMI), time spent working, time spend pursuing leisure activity, number of friends, acquaintances, and family members, aptitude battery, financial security, mental health, and the like. Processor 104 may generate an average longevity parameter using a machine-learning model.

Continuing in reference to FIG. 1, a "longevity level," as used in this disclosure, is an element of data relating to the predicted life span of a given system. In an embodiment, a longevity level 116 may predict the life span of a given system as a function of life energy, overall health, and performance metrics. Longevity level 116 may be qualitative elements such as binary elements, for instance a range of time a system can continue to function without failure. Longevity level 116 may also be expressed in a Boolean, 'yes' or 'no', 'true' or 'false', a category name, identifier, or that like, that may apply to any system that is a part Longevity measurement 108. In non-limiting illustrative examples, a Longevity level 116 may be calculated using qualitative elements such as the presence or absence of exercise, names of the types of activities as part of exercise, eating habits, BMI, substance abuse, lifestyle choices, and the like. Longevity level 116 may include quantitative elements represented, for instance and without limitation, as numerical values, polar coordinates, functions, matrices, and the like. In non-limiting illustrative examples, a Longevity level 116 may include quantitative elements such as used to describe how long a until a user's system will fail if the current lifestyle choices by the user are unchanged. Longevity level 116 may also be expressed in longevity scale. As used in the current disclosure, a "longevity scale" may be a scale score rating of how likely it is a user's system is to make it to a given age without failure. In non-limiting illustrative examples, A patient who has chronic kidney failure may receive a low scale score of living an additional 10 years without additional kidney failures. A longevity level paired with an actual age may be used to project a user's "actual life expectancy," defined as a probable age of system failure, as predicted using any method and/or table, and/or an interval from a date such as the present date to the probable age of death; actuarial methods may include looking up and/or calculating a user's life expectancy using date of birth and/or demographic information about the user such as sex, ethnicity, geographic location, nationality, or the like.

Still referring to FIG. 1, at least a processor 104 may be configured to provide a health impact factor. A "health impact factor," as used in this disclosure, is a calculation used to predict the impact a user's actions have on their health and/or actual life expectancy. Health impact factor may be a calculation used demonstrate the trajectory of a user's health if a certain activity is continued. Health Impact factor it may be multiplied by a user's actual age to determine the impact the actions have on the user's actual life expectancy. Activities that are positive or negative for a user's health may impact health impact factor. Examples of user activities may include diet considerations, exercise habits, substance abuse habits, tobacco abuse, alcohol abuse, sleep schedule, overall level of stress, mental health, and the like. Each of these habits may be given a multiplier number based on the user's activity. The multiplier may be determined by the longevity and severity of the activity when compared with the user's current health. In a non-limiting example, the action of working out multiple times a week over the course of 4 years may receive health impact factor of 1.25. This number may then be multiplied by the user's actual life expectancy to demonstrate a 25% addition in the user's life expectancy as a function of the activity. In other embodiments, a user may use harmful illegal drugs several times a week over many years. This may produce a health impact factor of 0.75. This number may then be multiplied by the user's actual life expectancy to demonstrate a 25% reduction in the users life expectancy. A users heath impact factor may increase or decrease based on the severity of the actions that are taken by the user. In an embodiment, generating a health impact factor may include identifying the habits of a user. The user habits may be identified by a user entry; for instance, and without limitation, at least a processor 104 may provide a user with a questionnaire in the form of one or more data fields requesting that the user identify activities in which the user engaged. Questions presented to a user may include a number of times that a user engages in physical activity during a given period of time such as a day, a week or a year. Questions may also be directed to the substance abuse and the severity of the said substance abuse. This may include questions about how much and how often a user's drinks alcohol or does illegal substances. A user's responses may be verified by an evaluation by a medical professional to ensure accuracy. A medical professional may look for overt signs of activities that may affect a user's health. For example, a user may indicate that they rarely smoke cigarettes, however upon physical examination of a user's lungs it is apparent that the user is a heavy smoker.

With continued reference to FIG. 1, Processor 104 may be configured to assign the user a longevity level 116 as a function of the classification of a longevity level 116 to a longevity parameter 112. Inputs to the to the longevity classifier 128 may include longevity measurement 108, longevity parameter 112, longevity level 116, rate of aging, average longevity parameter, age comparison metric, users longevity data, users anatomy data, and the like. The output to the classifier 128 may be a longevity level 116 that is specific to the given user. Longevity training data is a plurality of data entries containing a plurality of inputs that are correlated to a plurality of outputs for training a processor by a machine-learning process to align and classify attributes of a user's system to a longevity level 116. Longevity training data may be received from a database, such as training data database disclosed with reference to FIG. 4. Longevity training data may contain information about the longevity measurement 108, longevity parameter 112, longevity level 116, rate of aging, average longevity parameter, age comparison metric, user's anatomy data, health impact factor, actual age, and the like. Longevity training data may be generated from any past longevity measurement 108, longevity parameter 112, longevity level 116, rate of aging, average longevity parameter, age comparison metric, user's anatomy data, and the like. Longevity training data may correlate an example of a longevity parameter to an example of a longevity level. The "example of a longevity parameter" and the "example of a longevity level may be prior a prior longevity parameter and a prior longevity level, respectively. In other embodiments, longevity training data may be configured to correlate a longevity measurement 108 to a longevity parameter 112. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

With continued reference to FIG. 1, Processor 104 may be configured to calculate a longevity parameter 112 using a longevity machine learning model. Inputs to the machine learning model may include current longevity measurements 108, previous longevity measurements 108, previous longevity parameters 112, previous longevity levels 116, rate of aging, average longevity parameter, age comparison metric, user's anatomy data, longevity data, and the like. This data may be received from a database, such as longevity database 300. Previous longevity measurements 108, previous longevity parameter 112, and previous longevity levels 116 may come from the current user or users similarly situated to the users by health conditions, age, and fitness levels. Longevity machine learning model may be trained using training data such as prior longevity measurements and prior longevity parameters. Training data may be received from a database, such as training data database 400. The output of the longevity machine learning model may be a longevity parameter 112 that is specific to the given user.

With continued reference to FIG. 1, a classifier, such as longevity classifier 128, may be implemented as a fuzzy inferencing system. As used in the current disclosure, a "fuzzy inference" is a method that interprets the values in the input vector (i.e., longevity parameter 112 and longevity level 116) and, based on a set of rules, assigns values to the output vector. A set of Fuzzy rules may include a collection of linguistic statements that describe how the system should make a decision regarding classifying an input or controlling an output. While using fuzzy logic, the truth of any statement may become a matter of a degree. A fuzzy inference may include the process of mapping from a given input to an output using fuzzy logic. The mapping may then then provide a basis from which decisions can be made or patterns discerned. The process of fuzzy inference may involve functions, fuzzy logic operators, and if-then rules, etc. The system may be applied using two types of fuzzy inference systems: Mamdani-type and Sugeno-type. These two types of inference systems vary somewhat in the way outputs are determined.

Still referring to FIG. 1, processor 104 may be utilize a knowledge-based system (KBS) classify a user's longevity parameter 112 to a longevity level 116. As used in this disclosure, a KBS is a computer program that reasons and uses a knowledge base to solve complex problems. The KBS has two distinguishing features: a knowledge base and an inference engine. A knowledge base may include technology used to store complex structured and unstructured information used by a computer system, often in some form of subsumption ontology rather than implicitly embedded in procedural code. Other common approaches in addition to a subsumption ontology include frames, conceptual graphs, and logical assertions. In some embodiments, the knowledge base may be a storage hub that contains information about past matches of user's longevity parameter to a longevity level based on the similarity of inputs and feedback from users and medical professionals about the compatibility of matches. Next, an Inference engine allows new knowledge to be inferred. For example, the inference engine may determine that a user's system has a longevity parameter 112 similar to that of a on severely obese 50-year-old, the system may then infer that the user has or is susceptible to diseases associated with severe obesity (i.e. high blood pressure, diabetes, heart problems) Most commonly, it can take the form of IF-THEN rules coupled with forward chaining or backward chaining approaches. Forward chaining starts with the known facts and asserts new facts. Backward chaining starts with goals and works backward to determine what facts must be asserted so that the goals can be achieved. Other approaches include the use of automated theorem provers, logic programming, blackboard systems, and term rewriting systems such as CHR (Constraint Handling Rules). For example, following the IF-THEN rule format, the inference engine could devise "if user input consists of having a longevity parameter 112 in relations to their heart of 20 when the user has an actual age of 60 years old then that user input is compatible with the users having a longevity level 116 indicating a long and health life of the user's cardiovascular system". The inference engine may make predictions or decisions in optimizing classifying longevity parameters to a longevity level to a user without being explicitly programmed to do so. The inference engine may receive constant feedback and self-learn based on previous classifications, as described through this disclosure, and recommendations to further refine and strengthen its recommendations.

Still referring to FIG. 1, processor 104 may be configured to rank a plurality of longevity parameters 112 in order of most problematic to least problematic, wherein a rank of longevity levels is based on the similarity score. In some embodiments, generating the ranking may include linear regression techniques. Processor 104 may be designed and configured to create a machine-learning model using techniques for development of linear regression models. Linear regression models may include ordinary least squares regression, which aims to minimize the square of the difference between predicted outcomes and actual outcomes according to an appropriate norm for measuring such a difference (e.g., a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm 13 mounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g., a quadratic, cubic or higher-order equation) providing a best predicted output/actual output fit is sought; similar methods to those described above may be applied to minimize error functions, as will be apparent to persons skilled in the art upon reviewing the entirety of this disclosure.

Still referring to FIG. 1, processor 104 may be configured to use longevity classifier 128 to classify, as a function of ranking, the user longevity parameter to a longevity level. For example, processor 104 may take inputs of the ranked longevity parameters and sort into categories, selectable by user, such as: system, severity, level of risk, most correctable, and the like. In some embodiments, processor 104 may be configured to produce classification output results including the classified ranked longevity level in a selectable format by user, including at least the ranked longevity parameters and longevity levels with the similarity score displayed by each longevity level or longevity posting. For example, user may select to output classified ranked longevity parameters and longevity levels in a pie chart, wherein the ranked classified longevity parameters and longevity levels are divided, and color coded in selectable classification bins, showing the number of longevity parameters and longevity levels that fall into a classification.

Still referring to FIG. 1, processor may be configured to generate a classifier, such as longevity classifier 128, using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A) \div P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Processor 104 may then calculate a likelihood table by calculating probabilities of different data entries and classification labels. Processor 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 1, processor 104 may be configured to generate a classifier, such as longevity classifier 128, using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute/as derived using a Pythagorean norm:

$$l = \sqrt{\sum_{i=0}^{n} a_i^2},$$

where $a_i$ is attribute number experience of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values. Still referring to FIG. 1, processor 104 may be configured to generate a longevity plan 120. As used in the current disclosure, a "longevity plan" is a set of corrective measures that can improve a user's longevity level 116. Corrective measures may include a change in dietary habits, substance abuse, exercise habits, social habits, sleeping habits, and the like. Longevity plan 120 may include one or more modalities including but not limited to medical therapies, prescription medications, exercise, supplements, spirituality, and the like. For example, a longevity plan 120 may include the use of stem cell based therapies, anti-inflammatory drugs, blood-borne juvenile factors, elimination of damaged cells, telomerase reactivation, epigenetic drugs, activation of chaperones and protease systems, Mitohormetics, mitophagy, clearance of senescent cells, IIS and mTOR inhibition, AMK and sirtins activation. The longevity plan 120 may be monitored in conjunction with one or more longevity parameters 112 or longevity measurements 108 to provide feedback to a user and determine any adjustments and/or modifications. The information gathered from as a result of monitoring the effects of a longevity plan 120 may then be used in a feedback loop to determine a new longevity parameter 112 or longevity level 116 based on how a user progresses through a particular program. The new longevity parameter 112 and/or longevity level may be used to generate a new longevity plan 120 or update the existing longevity plan 120.

With continued reference to FIG. 1, Processor 104 may be configured to calculate a longevity plan 120 using a machine learning model. Inputs to the machine learning model may include past or present longevity measurements 108, longevity parameters 112, longevity levels 116, rate of aging, average longevity parameter, age comparison metric, user's anatomy data, longevity data, and the like. This data may be received from a database, such as longevity database 300. Previous longevity measurements 108, previous longevity parameter 112, and previous longevity levels 116 may come from the current user or users similarly situated to the users by health conditions, age, and fitness levels. Inputs into the machine learning model may also include the output of the longevity machine learning model and/or longevity classifier 128. The output of the machine learning model may be a longevity level 120 that is specific to the given user. The machine learning model may be trained using longevity training data. Longevity training data is a plurality of data entries containing a plurality of inputs that are correlated to a plurality of outputs for training a processor by a machine-learning process to generate a longevity measurement 108.

With continued reference to FIG. 1, in some embodiments, apparatus 100 may receive survey data from a patient. The survey data may include responses to a patient survey given to a patient. The survey may include questions regarding the patient's growth mindset, mental health, feeling of safety, feeling of being loved, energy levels, life purpose, health of relationships, feelings of joy, spiritual health, and the like. The survey data may be used at various points by apparatus 100. For example, the survey data may be a component of longevity measurement 108. In some embodiments, survey data may be used to generate longevity parameter 112 or determine longevity level. For example, if the user reports a loss of energy, that may indicate increased aging. Additionally, survey data may be used to tailor or update longevity plan 120. For example if a user reports a loss of energy or decreased stability in their mental health, which may indicate that longevity plan 120 needs to be altered in order to better fit the user.

Referring again to FIG. 1, apparatus 100 may further include a Data storage device 124. Data storage device 124 may be communicatively connected to processor 104 and may be configured to store, information related to longevity measurement 108, longevity parameter 112, longevity level 116, longevity plan 120, rate of aging, average longevity parameter, age comparison metric, user's anatomy data, and the like. In one or more embodiments, Data storage device 124 is communicatively connected to a processor. For example, Data storage device 124 may store previously prepared records (e.g., longevity plans), records generated by processor 104, longevity parameter 112, longevity level 116, longevity plan 120, and the like. In one or more embodiments, memory component may include a storage device, as described further in this disclosure below. Data storage device 124 may be consistent with longevity database 300 disclosed with reference to FIG. 3 and/or training data database 400 disclosed with reference to FIG. 4.

With continued reference to FIG. 1, longevity level 116, longevity parameter 112, and longevity plan 120 may be displayed using a GUI. GUI may include a plurality of lines, images, symbols. GUI may be displayed on a display device. Display device may include, but is not limited to, a smartphone, tablet, laptop, monitor, tablet, and the like. Display device may include a separate device that includes a transparent screen configured to display computer generated images and/or information. The user may view the information displayed on the display device in real time.

Figure 2:
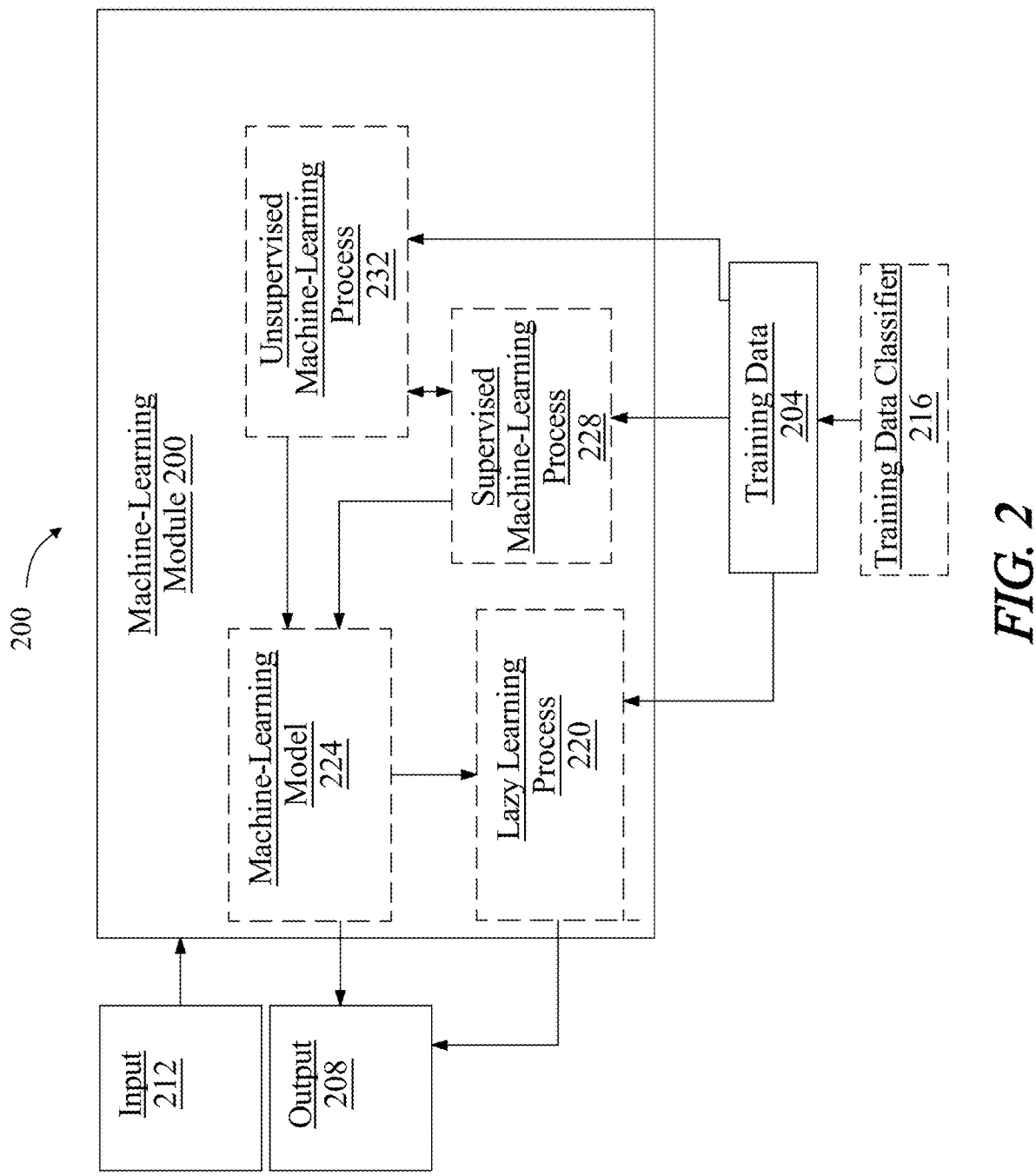
FIG. 2 is a block diagram of an exemplary machine-learning process.

Referring now to FIG. 2, an exemplary embodiment of a machine-learning module 200 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 204 to generate an algorithm that will be performed by a computing device/module to produce outputs 208 given data provided as inputs 212; this is in contrast to a non-machine learning software program where the commands to be executed are determined in advance by a user and written in a programming language.

Still referring to FIG. 2, "training data," as used herein, is data containing correlations that a machine-learning process may use to model relationships between two or more categories of data elements. For instance, and without limitation, training data 204 may include a plurality of data entries, each entry representing a set of data elements that were recorded, received, and/or generated together; data elements may be correlated by shared existence in a given data entry, by proximity in a given data entry, or the like. Multiple data entries in training data 204 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 204 according to various correlations; correlations may indicate causative and/or predictive links between categories of data elements, which may be modeled as relationships such as mathematical relationships by machine-learning processes as described in further detail below. Training data 204 may be formatted and/or organized by categories of data elements, for instance by associating data elements with one or more descriptors corresponding to categories of data elements. As a non-limiting example, training data 204 may include data entered in standardized forms by persons or processes, such that entry of a given data element in a given field in a form may be mapped to one or more descriptors of categories. Elements in training data 204 may be linked to descriptors of categories by tags, tokens, or other data elements; for instance, and without limitation, training data 204 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 2, training data 204 may include one or more elements that are not categorized; that is, training data 204 may not be formatted or contain descriptors for some elements of data. Machine-learning algorithms and/or other processes may sort training data 204 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 204 to be made applicable for two or more distinct machine-learning algorithms as described in further detail below. Training data 204 used by machine-learning module 200 may correlate any input data as described in this disclosure to any output data as described in this disclosure. As a non-limiting illustrative example inputs may include longevity measurement 108 and outputs may include longevity parameter 112 As another non-limiting example, inputs may include longevity parameter 112 and/or longevity measurement 108 and outputs may include longevity level 116. As another non-limiting example, inputs may include longevity parameter 112 and/or longevity level 116, and outputs may include longevity plan 120.

Further referring to FIG. 2, training data may be filtered, sorted, and/or selected using one or more supervised and/or unsupervised machine-learning processes and/or models as described in further detail below; such models may include without limitation a training data classifier 216. Training data classifier 216 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 200 may generate a classifier using a classification algorithm, defined as a processes whereby a computing device and/or any module and/or component operating thereon derives a classifier from training data 204. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 216 may classify elements of training data to ages of patients, health of patients, actual age of patients, and/or health history of patients.

Still referring to FIG. 2, machine-learning module 200 may be configured to perform a lazy-learning process 220 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 204. Heuristic may include selecting some number of highest-ranking associations and/or training data 204 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 2, machine-learning processes as described in this disclosure may be used to generate machine-learning models 224. A "machine-learning model," as used in this disclosure, is a mathematical and/or algorithmic representation of a relationship between inputs and outputs, as generated using any machine-learning process including without limitation any process as described above and stored in memory; an input is submitted to a machine-learning model 224 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 224 may be generated by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 2, machine-learning algorithms may include at least a supervised machine-learning process 228. At least a supervised machine-learning process 228, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include inputs as described above in this disclosure as inputs, outputs as described above in this disclosure as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 204. Persons skilled in the art, upon reviewing the entirety of this disclosure, will be aware of various possible variations of at least a supervised machine-learning process 228 that may be used to determine relation between inputs and outputs. Supervised machine-learning processes may include classification algorithms as defined above.

Further referring to FIG. 2, machine learning processes may include at least an unsupervised machine-learning processes 232. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 2, machine-learning module 200 may be designed and configured to create a machine-learning model 224 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Figure 3:
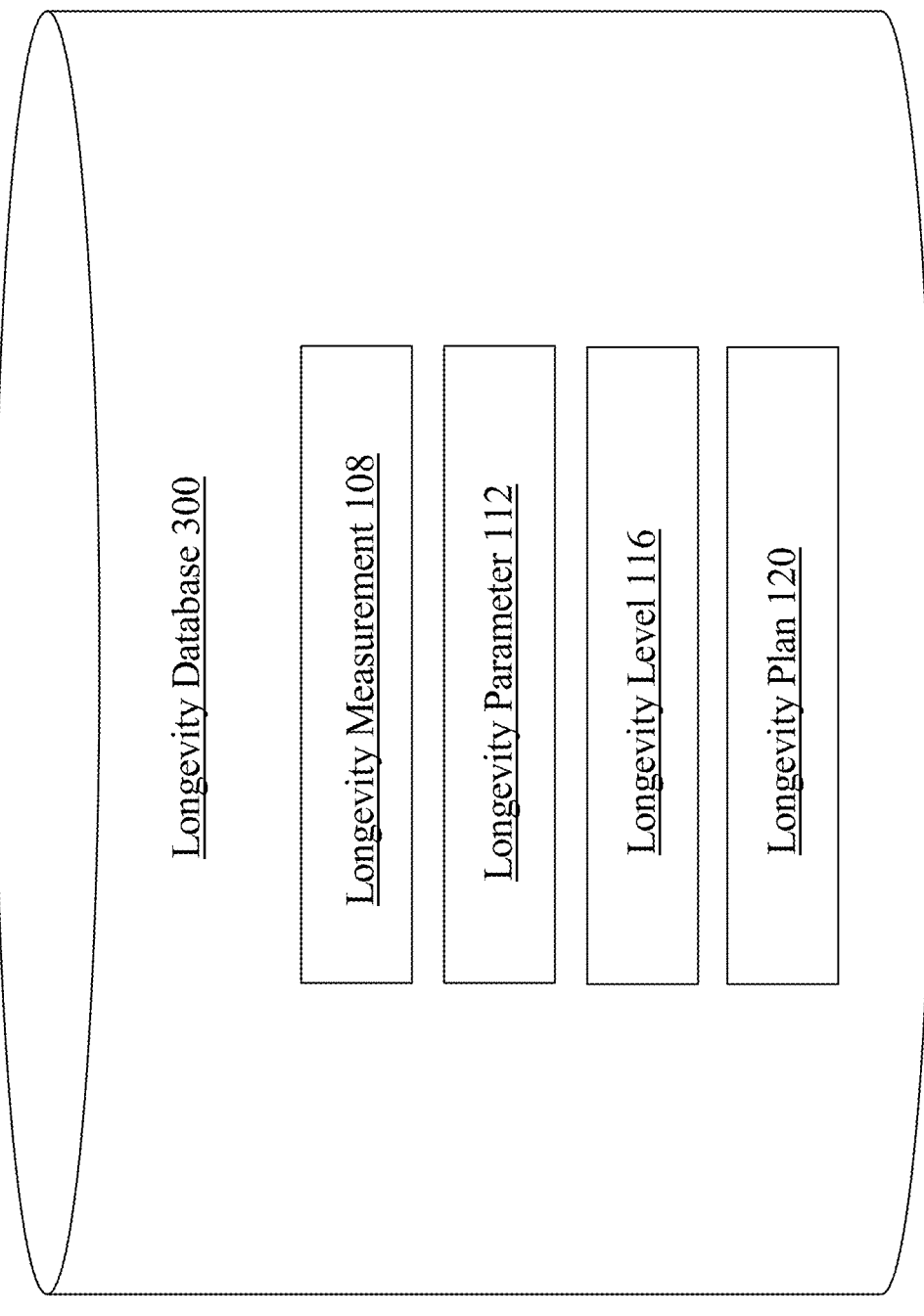
FIG. 3 is a block diagram of an exemplary embodiment of a longevity database.

Now referring to FIG. 3, an exemplary longevity database 300 is illustrated by way of block diagram. Longevity measurement 108, longevity level 116, longevity parameter 112, and/or longevity plan 120 may be stored in a longevity database 300 (also referred to as "database"). Processor 104 may be communicatively connected with longevity database 300. For example, in some cases, database 300 may be local to processor 104. Alternatively or additionally, in some cases, database 300 may be remote to processor 104 and communicative with processor 104 by way of one or more networks. Network may include, but not limited to, a cloud network, a mesh network, or the like. By way of example, a "cloud-based" system, as that term is used herein, can refer to a system which includes software and/or data which is stored, managed, and/or processed on a network of remote servers hosted in the "cloud," e.g., via the Internet, rather than on local severs or personal computers. A "mesh network" as used in this disclosure is a local network topology in which the infrastructure processor 104 connect directly, dynamically, and non-hierarchically to as many other computing devices as possible. A "network topology" as used in this disclosure is an arrangement of elements of a communication network. Longevity database 300 may be implemented, without limitation, as a relational database, a key-value retrieval database such as a NOSQL database, or any other format or structure for use as a database that a person skilled in the art would recognize as suitable upon review of the entirety of this disclosure. Longevity database 300 may alternatively or additionally be implemented using a distributed data storage protocol and/or data structure, such as a distributed hash table or the like. Longevity database 300 may include a plurality of data entries and/or records as described above. Data entries in a database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure.

Figure 4:
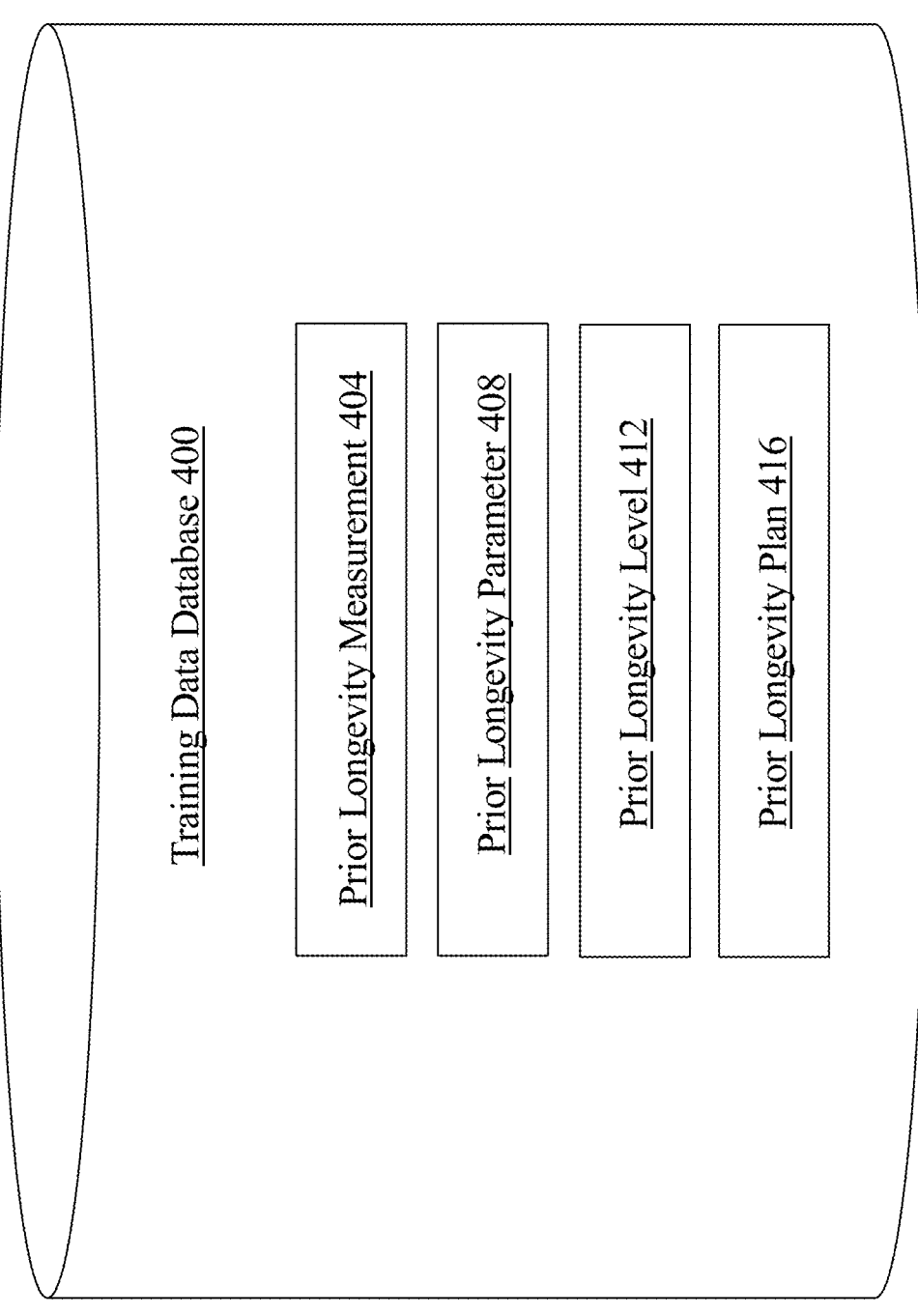
FIG. 4 is a block diagram of an exemplary embodiment of a training data database.

Referring now to FIG. 4, training data database 400 may store a prior longevity measurement 404, prior longevity parameter 408, prior longevity level 412, and/or prior longevity plan. Prior longevity measurement 404 may be a longevity measurement 108 from a previous user, or a longevity measurement 108 collected at a prior time. Prior longevity parameter 408 may be a longevity parameter 112 from a previous user, or a longevity parameter 112 collected at a prior time. Prior longevity level 412 may be a longevity level 116 from a previous user, or a longevity level 116 collected at a prior time. Prior longevity plan 416 may be a longevity plan 120 from a previous user, or a longevity plan 120 collected at a prior time. In general, training data database may store any training data that processor 104 may require. Processor 104 may be communicatively connected with training data database 400. For example, in some cases, training data database 400 may be local to processor 104. Alternatively or additionally, in some cases, training data database 400 may be remote to processor 104 and communicative with processor 104 by way of one or more networks. Network may include, but not limited to, a cloud network, a mesh network, or the like. Training data database 400 may be implemented, without limitation, as a relational database, a key-value retrieval database such as a NOSQL database, or any other format or structure for use as a database that a person skilled in the art would recognize as suitable upon review of the entirety of this disclosure. Training data database 400 may alternatively or additionally be implemented using a distributed data storage protocol and/or data structure, such as a distributed hash table or the like. Training data database 400 may include a plurality of data entries and/or records as described above. Data entries in a database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure.

Figure 5:
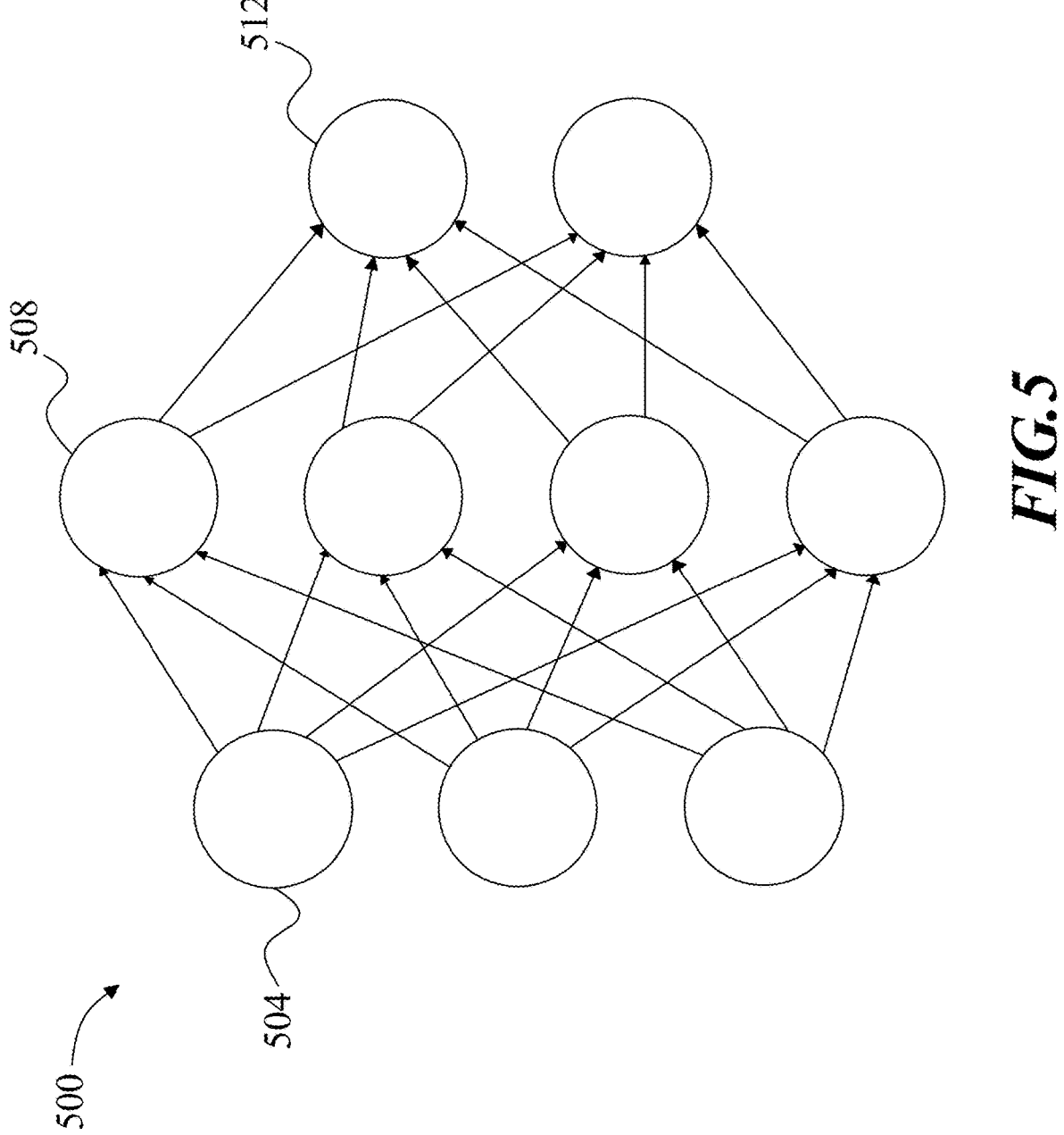
FIG. 5 is a diagram of an exemplary embodiment of neural network.

Referring now to FIG. 5, an exemplary embodiment of neural network 500 is illustrated. A neural network 500 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 504, one or more intermediate layers 508, and an output layer of nodes 512. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 6:
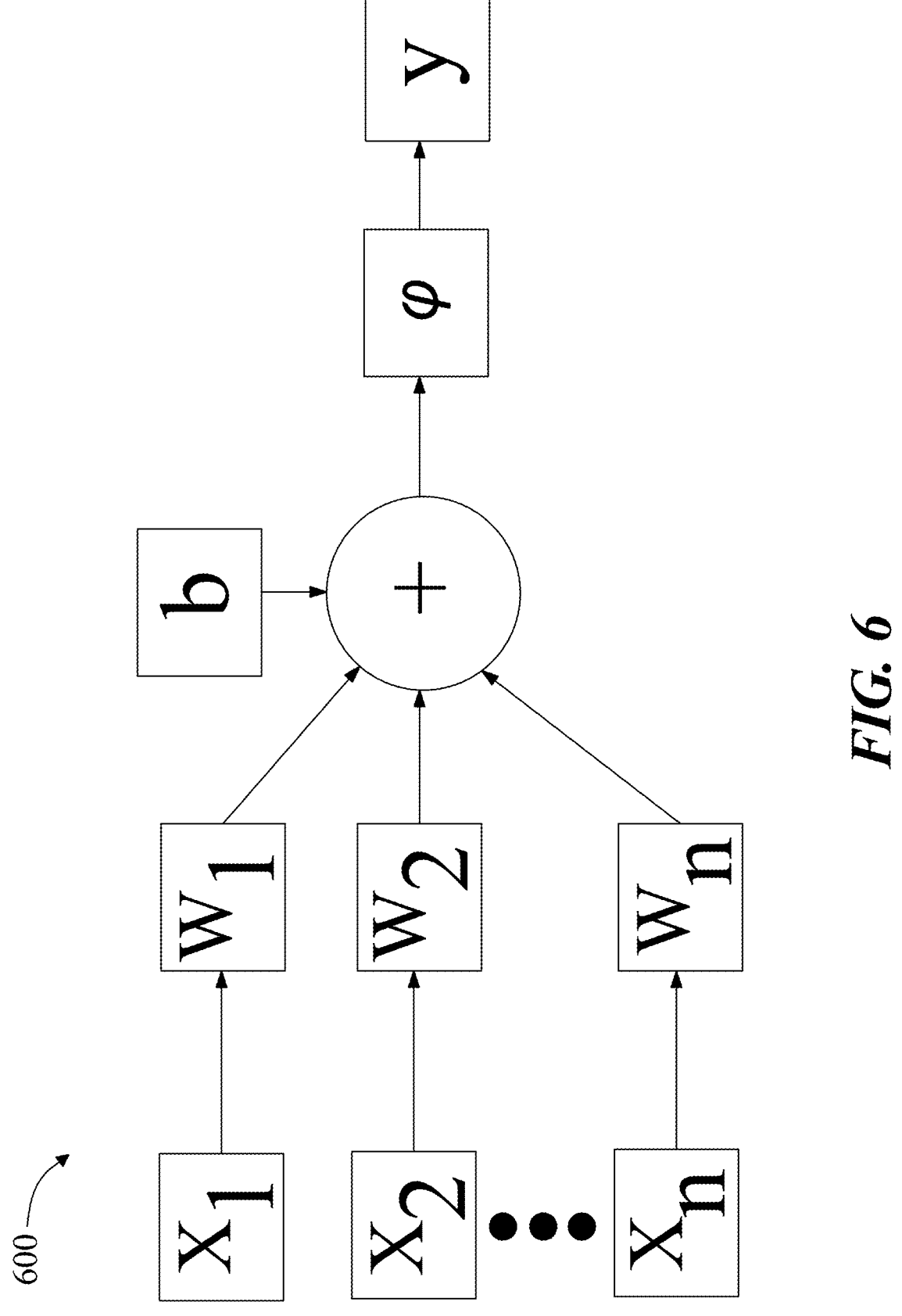
FIG. 6 is a diagram of an exemplary embodiment of a node of a neural network.

Referring now to FIG. 6, an exemplary embodiment of a node of a neural network is illustrated. A node may include, without limitation a plurality of inputs $x_i$ that may receive numerical values from inputs to a neural network containing the node and/or from other nodes. Node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Figure 7:
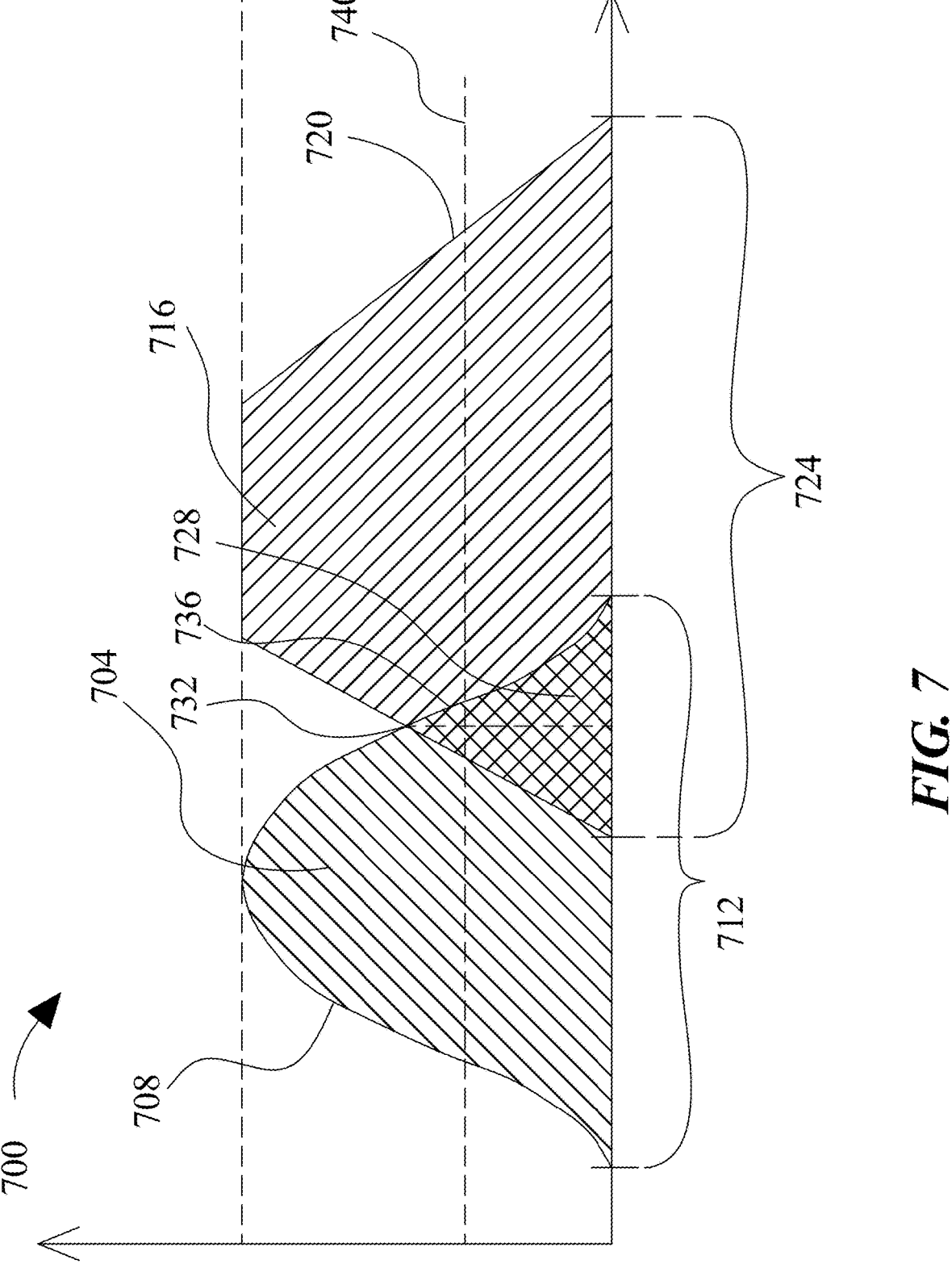
FIG. 7 is a graph illustrating an exemplary relationship between fuzzy sets.

Now referring to FIG. 7, an exemplary embodiment of fuzzy set comparison 700 is illustrated. In a non-limiting embodiment, the fuzzy set comparison. In a non-limiting embodiment, fuzzy set comparison 700 may be consistent with fuzzy set comparison in FIG. 1. In another non-limiting the fuzzy set comparison 700 may be consistent with the name/version matching as described herein. For example and without limitation, the parameters, weights, and/or coefficients of the membership functions may be tuned using any machine-learning methods for the name/version matching as described herein. In another non-limiting embodiment, the fuzzy set may represent longevity levels 116 and longevity parameters 112 from FIG. 1.

Alternatively or additionally, and still referring to FIG. 7, fuzzy set comparison 700 may be generated as a function of determining data compatibility threshold. The compatibility threshold may be determined by a computing device. In some embodiments, a computing device may use a logic comparison program, such as, but not limited to, a fuzzy logic model to determine the compatibility threshold and/or version authenticator. Each such compatibility threshold may be represented as a value for a posting variable representing the compatibility threshold, or in other words a fuzzy set as described above that corresponds to a degree of compatibility and/or allowability as calculated using any statistical, machine-learning, or other method that may occur to a person skilled in the art upon reviewing the entirety of this disclosure. In some embodiments, determining the compatibility threshold and/or version authenticator may include using a linear regression model. A linear regression model may include a machine learning model. A linear regression model may map statistics such as, but not limited to, frequency of the same range of version numbers, and the like, to the compatibility threshold and/or version authenticator. In some embodiments, determining the compatibility threshold of any posting may include using a classification model. A classification model may be configured to input collected data and cluster data to a centroid based on, but not limited to, frequency of appearance of the range of versioning numbers, linguistic indicators of compatibility and/or allowability, and the like. Centroids may include scores assigned to them such that the compatibility threshold may each be assigned a score. In some embodiments, a classification model may include a K-means clustering model. In some embodiments, a classification model may include a particle swarm optimization model. In some embodiments, determining a compatibility threshold may include using a fuzzy inference engine. A fuzzy inference engine may be configured to map one or more compatibility threshold using fuzzy logic. In some embodiments, a plurality of computing devices may be arranged by a logic comparison program into compatibility arrangements. A "compatibility arrangement" as used in this disclosure is any grouping of objects and/or data based on skill level and/or output score. Membership function coefficients and/or constants as described above may be tuned according to classification and/or clustering algorithms. For instance, and without limitation, a clustering algorithm may determine a Gaussian or other distribution of questions about a centroid corresponding to a given compatibility threshold and/or version authenticator, and an iterative or other method may be used to find a membership function, for any membership function type as described above, that minimizes an average error from the statistically determined distribution, such that, for instance, a triangular or Gaussian membership function about a centroid representing a center of the distribution that most closely matches the distribution. Error functions to be minimized, and/or methods of minimization, may be performed without limitation according to any error function and/or error function minimization process and/or method as described in this disclosure.

Still referring to FIG. 7, inference engine may be implemented according to input and/or output longevity level 116 and longevity parameter 112. For instance, an acceptance variable may represent a first measurable value pertaining to the classification of longevity parameter 112 to longevity level 116. Continuing the example, an output variable may represent a longevity level 116 as it relates to the current user. In an embodiment, longevity level 116 and longevity parameter 112 may be represented by their own fuzzy set. In other embodiments, a longevity level 116 specific to the user may be represented as a function of the intersection two fuzzy sets as shown in FIG. 7, An inference engine may combine rules, such as any semantic versioning, semantic language, version ranges, and the like thereof. The degree to which a given input function membership matches a given rule may be determined by a triangular norm or "T-norm" of the rule or output function with the input function, such as min (a, b), product of a and b, drastic product of a and b, Hamacher product of a and b, or the like, satisfying the rules of commutativity (T(a, b)=T(b, a)), monotonicity: (T(a, b)≤T(c, d) if a≤c and b≤d), (associativity: T(a, T(b, c))=T (T(a, b), c)), and the requirement that the number 1 acts as an identity element. Combinations of rules ("and" or "or" combination of rule membership determinations) may be performed using any T-conorm, as represented by an inverted T symbol or "⊥" such as max(a, b), probabilistic sum of a and b (a+b−a*b), bounded sum, and/or drastic T-conorm; any T-conorm may be used that satisfies the properties of commutativity: ⊥(a, b)=⊥(b, a), monotonicity: ⊥(a, b)≤⊥(c, d) if a≤c and b≤d, associativity: ⊥(a, ⊥(b, c))=⊥(⊥(a, b), c), and identity element of 0. Alternatively or additionally T-conorm may be approximated by sum, as in a "product-sum" inference engine in which T-norm is product and T-conorm is sum. A final output score or other fuzzy inference output may be determined from an output membership function as described above using any suitable defuzzification process, including without limitation Mean of Max defuzzification, Centroid of Area/Center of Gravity defuzzification, Center Average defuzzification, Bisector of Area defuzzification, or the like. Alternatively or additionally, output rules may be replaced with functions according to the Takagi-Sugeno-King (TSK) fuzzy model.

A first fuzzy set 704 may be represented, without limitation, according to a first membership function 708 representing a probability that an input falling on a first range of values 712 is a member of the first fuzzy set 704, where the first membership function 708 has values on a range of probabilities such as without limitation the interval [0,1], and an area beneath the first membership function 708 may represent a set of values within first fuzzy set 704. Although first range of values 712 is illustrated for clarity in this exemplary depiction as a range on a single number line or axis, first range of values 712 may be defined on two or more dimensions, representing, for instance, a Cartesian product between a plurality of ranges, curves, axes, spaces, dimensions, or the like. First membership function 708 may include any suitable function mapping first range 712 to a probability interval, including without limitation a triangular function defined by two linear elements such as line segments or planes that intersect at or below the top of the probability interval. As a non-limiting example, triangular membership function may be defined as:

$$y(x, a, b, c) = \begin{cases} 0, \text{ for } x > c \text{ and } x < a \\ \dfrac{x-a}{b-a}, \text{ for } a \le x < b \\ \dfrac{c-x}{c-b}, \text{ if } b < x \le c \end{cases}$$

a trapezoidal membership function may be defined as:

$$y(x, a, b, c, d) = \max\left(\min\left(\dfrac{x-a}{b-a}, 1, \dfrac{d-x}{d-c}\right), 0\right)$$

a sigmoidal function may be defined as:

$$y(x, a, c) = \dfrac{1}{1 - e^{-a(x-c)}}$$

a Gaussian membership function may be defined as:

$$y(x, c, \sigma) = e^{-\frac{1}{2}\left(\frac{x-c}{\sigma}\right)^2}$$

and a bell membership function may be defined as:

$$y(x, a, b, c,) = \left[1 + \left|\dfrac{x-c}{a}\right|^{2b}\right]^{-1}$$

Persons skilled in the art, upon reviewing the entirety of this disclosure, will be aware of various alternative or additional membership functions that may be used consistently with this disclosure.

First fuzzy set 704 may represent any value or combination of values as described above, including any software component datum, any source repository datum, any malicious quantifier datum, any predictive threshold datum, any string distance datum, any resource datum, any niche datum, and/or any combination of the above. A second fuzzy set 716, which may represent any value which may be represented by first fuzzy set 704, may be defined by a second membership function 720 on a second range 724; second range 724 may be identical and/or overlap with first range 712 and/or may be combined with first range via Cartesian product or the like to generate a mapping permitting evaluation overlap of first fuzzy set 704 and second fuzzy set 716. Where first fuzzy set 704 and second fuzzy set 716 have a region 736 that overlaps, first membership function 708 and second membership function 720 may intersect at a point 732 representing a probability, as defined on probability interval, of a match between first fuzzy set 704 and second fuzzy set 716. Alternatively or additionally, a single value of first and/or second fuzzy set may be located at a locus 736 on first range 712 and/or second range 724, where a probability of membership may be taken by evaluation of first membership function 708 and/or second membership function 720 at that range point. A probability at 728 and/or 732 may be compared to a threshold 740 to determine whether a positive match is indicated. Threshold 740 may, in a non-limiting example, represent a degree of match between first fuzzy set 704 and second fuzzy set 716, and/or single values therein with each other or with either set, which is sufficient for purposes of the matching process; for instance, longevity level 116 may indicate a sufficient degree of overlap with the longevity parameter 112 for combination to occur as described above. There may be multiple thresholds; for instance, a second threshold may indicate a sufficient match for purposes of past posting and posting query as described in this disclosure. Each threshold may be established by one or more user inputs. Alternatively or additionally, each threshold may be tuned by a machine-learning and/or statistical process, for instance and without limitation as described in further detail below.

In an embodiment, a degree of match between fuzzy sets may be used to rank one resource against another. For instance, if both longevity level 116 and longevity parameter 112 have fuzzy sets matching a longevity level fuzzy set by having a degree of overlap exceeding a predictive threshold, processor 104 may further rank the two resources by ranking a resource having a higher degree of match more highly than a resource having a lower degree of match. Where multiple fuzzy matches are performed, degrees of match for each respective fuzzy set may be computed and aggregated through, for instance, addition, averaging, or the like, to determine an overall degree of match, which may be used to rank resources; selection between two or more matching resources may be performed by selection of a highest-ranking resource, and/or multiple notifications may be presented to a user in order of ranking.

Referring now to FIG. 8, an exemplary method 800 for enhancing longevity is illustrated. Method 800 includes a step 805, of receiving, using a processor, a longevity measurement related to a user, without limitation, as described above in reference to FIGS. 1-7. In some embodiments, the longevity measurement may include a biomarker associated with aging. Biomarkers associated with aging are described further with respect to FIG. 1. In some embodiments, step 805 of receiving the longevity measurement may include receiving the longevity measurement from a longevity database. This may be implemented, without limitation, as described above with reference to FIGS. 1-7. As an example, longevity database may be consistent with longevity database 300 described with reference to FIG. 3.

With continued reference to FIG. 8, method 800 includes a step 810 of calculating, using the processor, a longevity parameter as a function of the longevity measurement. This may be implemented, without limitation, as described above with reference to FIGS. 1-7. In some embodiments, the longevity parameter may include an age comparison metric for a user's system. In some embodiments, the longevity parameter may comprise a rate of aging.

With continued reference to FIG. 8, method 800 includes a step 815 of training, using the processor, a longevity classifier using a longevity training data wherein the longevity training data contains a plurality of data entries correlating examples of longevity parameters to examples of longevity levels. This may be implemented, without limitation, as described above with reference to FIGS. 1-7. In some embodiments, the longevity training data may include prior longevity measurement 404 and/or prior longevity parameter 408 of training data database 400. In some embodiments, step 815 may include receiving the longevity training data from a training data database. This may be implemented, without limitation, as described above with reference to FIGS. 1-7.

With continued reference to FIG. 8, method 800 includes a step 820 of classifying, using the processor, the longevity parameter to the longevity level using the longevity classifier. This may be implemented, without limitation, as described above with reference to FIGS. 1-7. In some embodiments, the longevity level may include a predicted life span of a given system. In some embodiments, step 820 may comprise assigning the longevity level as a function of a fuzzy inference. This may be implemented, without limitation, as described above with reference to FIGS. 1-7. In some embodiments, step 820 may include assigning the longevity level using a knowledge-based system. This may be implemented, without limitation, as described above with reference to FIGS. 1-7.

With continued reference to FIG. 8, method 800 includes a step 825 of assigning, using the processor, the user the longevity level as a function of the classification. In some embodiments, step 825 may comprise assigning the longevity level as a function of a rate of aging. This may be implemented, without limitation, as described above with reference to FIGS. 1-7.

With continued reference to FIG. 8, method 800 includes a step 830 of generating, using the processor, a longevity plan as a function of the longevity parameter and longevity level. This may be implemented, without limitation, as described above with reference to FIGS. 1-7. In some embodiments the longevity plan may include a set of corrective measures configured to improve the user's longevity level. In some embodiments, step 830 may include generating the longevity plan as a function of survey data.

With continued reference to FIG. 8, in some embodiments, method 800 may include receiving survey data from a user. This may be implemented, without limitation, as described above with reference to FIGS. 1-7. Method 800 may further include a step of updating the longevity plan as a function of the survey data. This may be implemented, without limitation, as described above with reference to FIGS. 1-7.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 9:
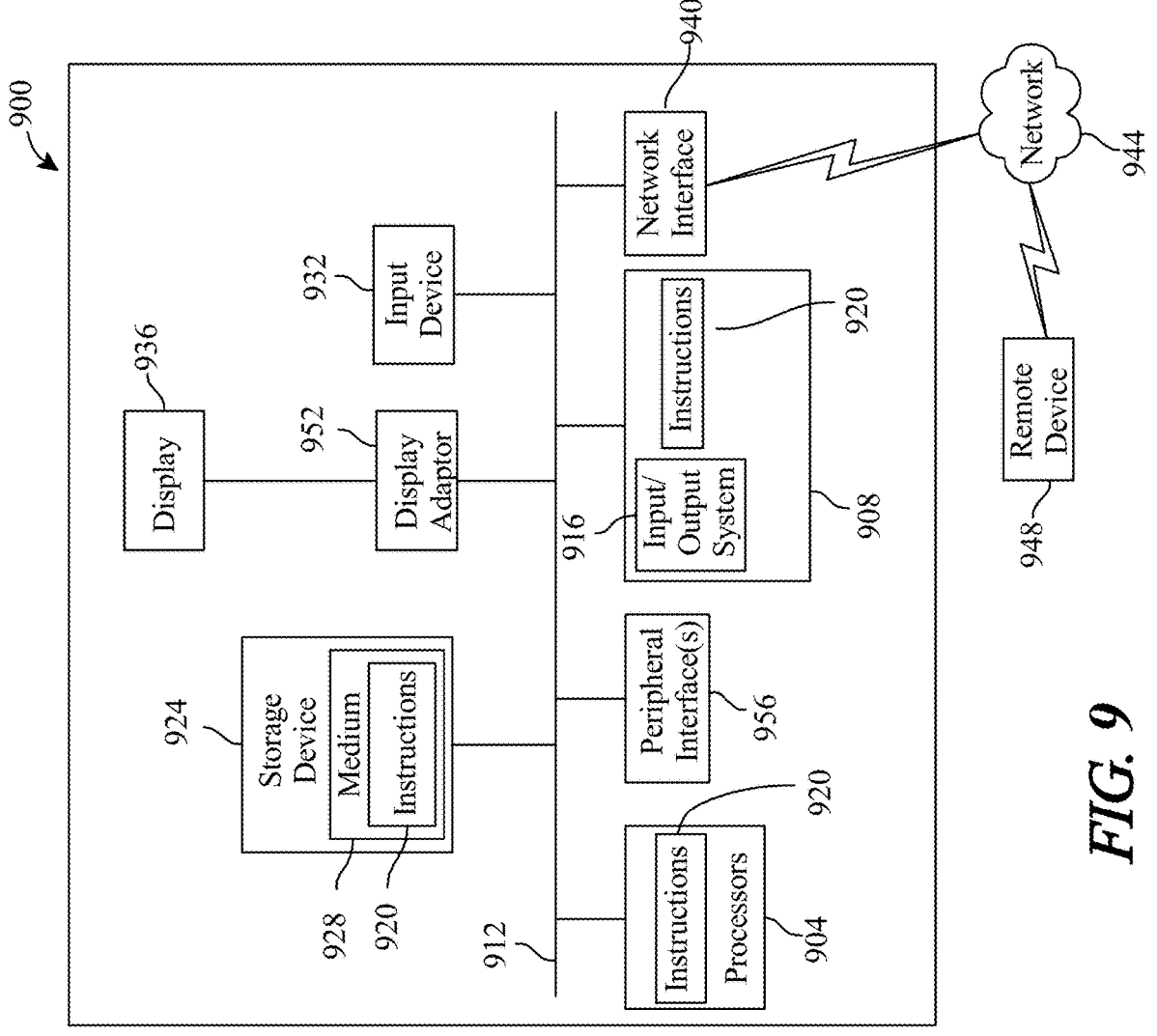
FIG. 9 is a block diagram of a computing system that can be used to implement any one or more of the methodologies disclosed herein and any one or more portions thereof.

FIG. 9 shows a diagrammatic representation of one embodiment of a computing device in the exemplary form of a computer system 900 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 900 includes a processor 904 and a memory 908 that communicate with each other, and with other components, via a bus 912. Bus 912 may include any of several types of bus structures including, but not limited to, a memory bus, a memory controller, a peripheral bus, a local bus, and any combinations thereof, using any of a variety of bus architectures.

Processor 904 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 904 may be organized according to Von Neumann and/or Harvard architecture as a non-limiting example. Processor 904 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 908 may include various components (e.g., machine-readable media) including, but not limited to, a random-access memory component, a read only component, and any combinations thereof. In one example, a basic input/output system 916 (BIOS), including basic routines that help to transfer information between elements within computer system 900, such as during start-up, may be stored in memory 908. Memory 908 may also include (e.g., stored on one or more machine-readable media) instructions (e.g., software) 920 embodying any one or more of the aspects and/or methodologies of the present disclosure. In another example, memory 908 may further include any number of program modules including, but not limited to, an operating system, one or more application programs, other program modules, program data, and any combinations thereof.

Computer system 900 may also include a storage device 924. Examples of a storage device (e.g., storage device 924) include, but are not limited to, a hard disk drive, a magnetic disk drive, an optical disc drive in combination with an optical medium, a solid-state memory device, and any combinations thereof. Storage device 924 may be connected to bus 912 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 924 (or one or more components thereof) may be removably interfaced with computer system 900 (e.g., via an external port connector (not shown)). Particularly, storage device 924 and an associated machine-readable medium 928 may provide nonvolatile and/or volatile storage of machine-readable instructions, data structures, program modules, and/or other data for computer system 900. In one example, software 920 may reside, completely or partially, within machine-readable medium 928. In another example, software 920 may reside, completely or partially, within processor 904.

Computer system 900 may also include an input device 932. In one example, a user of computer system 900 may enter commands and/or other information into computer system 900 via input device 932. Examples of an input device 932 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 932 may be interfaced to bus 912 via any of a variety of interfaces (not shown) including, but not limited to, a serial interface, a parallel interface, a game port, a USB interface, a FIRE-WIRE interface, a direct interface to bus 912, and any combinations thereof. Input device 932 may include a touch screen interface that may be a part of or separate from display 936, discussed further below. Input device 932 may be utilized as a user selection device for selecting one or more graphical representations in a graphical interface as described above.

A user may also input commands and/or other information to computer system 900 via storage device 924 (e.g., a removable disk drive, a flash drive, etc.) and/or network interface device 940. A network interface device, such as network interface device 940, may be utilized for connecting computer system 900 to one or more of a variety of networks, such as network 944, and one or more remote devices 948 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 944, may employ a wired and/or a wireless mode of communication. In general, any network topology may be used. Information (e.g., data, software 920, etc.) may be communicated to and/or from computer system 900 via network interface device 940.

Computer system 900 may further include a video display adapter 952 for communicating a displayable image to a display device, such as display device 936. Examples of a display device include, but are not limited to, a liquid crystal display (LCD), a cathode ray tube (CRT), a plasma display, a light emitting diode (LED) display, and any combinations thereof. Display adapter 952 and display device 936 may be utilized in combination with processor 904 to provide graphical representations of aspects of the present disclosure. In addition to a display device, computer system 900 may include one or more other peripheral output devices including, but not limited to, an audio speaker, a printer, and any combinations thereof. Such peripheral output devices may be connected to bus 912 via a peripheral interface 956. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions, and additions may be made to that which is specifically disclosed herein without departing from the spirit and scope of the present invention.

What is claimed is:

1. An apparatus for enhancing longevity, wherein the apparatus comprises:

at least a processor; and a memory communicatively connected to the at least a processor, the memory containing instructions configuring the at least a processor to:

receive a longevity measurement comprising at least a complete blood count related to a user;

provide a health impact factor, wherein the health impact factor is a function of the longevity measurement, and wherein the longevity measurement further comprises at least a historical longevity parameter;

calculate a longevity parameter as a function of the longevity measurement and the health impact factor;

assign the user a longevity level as a function of the longevity parameter, wherein the longevity level comprises a likelihood that a system of the user will make it to a given age without failure and wherein assigning the user the longevity level further comprises:

training a longevity machine learning model to generate a longevity classifier using a longevity training data, wherein the longevity training data contains a plurality of data entries correlating examples of longevity parameters to examples of longevity levels;

classifying the longevity parameter to the longevity level using the longevity classifier;

assigning the user the longevity level as a function of the classification, wherein assigning the longevity level further comprises utilizing a knowledge-based system (KBS), wherein utilizing the KBS comprises:

classifying the longevity parameter to the longevity level based on an if-then rule format, using an inference engine of the KBS;

updating the KBS based on previous longevity level classifications from the longevity machine learning model; and classifying an updated longevity parameter to an updated longevity level, using an updated inference engine of the KBS, wherein a knowledge base of the KBS stores rules and longevity data in a subsumption ontology distinct from implicitly embedded procedural code and wherein the inference engine utilizes forward chaining to assert new facts from known facts and backward chaining to determine additional facts required to achieve a goal longevity level; and generate a longevity plan as a function of the updated longevity parameter and the updated longevity level, wherein generating the longevity plan comprises:

receiving first training data correlating input data, the input data including longevity levels, to longevity plan data;

training a neural network using the first training data, wherein the neural network is configured to output the longevity plan;

outputting the longevity plan to the user;

receiving user feedback regarding effects of the longevity plan;

receiving survey data related to a user's health after monitoring the longevity plan;

updating the longevity plan based on the user feedback and the survey data; and using the updated longevity plan as training data to train the neural network.

2. The apparatus of claim 1, wherein the longevity parameter comprises an age comparison metric for the system of the user.

3. The apparatus of claim 1, wherein the longevity parameter comprises a rate of aging.

4. The apparatus of claim 1, wherein the longevity measurement comprises a biomarker associated with aging.

5. The apparatus of claim 1, wherein the longevity level comprises a predicted life span of a given system.

6. The apparatus of claim 1, wherein the longevity level is assigned as a function of a fuzzy inference.

7. The apparatus of claim 1, wherein the longevity plan comprises a set of corrective measures configured to improve the user's longevity level.

8. The apparatus of claim 1, wherein assigning the user the longevity level is a function of a rate of aging.

9. The apparatus of claim 1, wherein receiving the longevity measurement related to the user comprises receiving the longevity measurement from a longevity database.

10. A method for enhancing longevity, wherein the method comprises:

receiving, using a processor, a longevity measurement comprising at least a complete blood count related to a user;

providing, using the processor, a health impact factor wherein the health impact factor is a function of the longevity measurement, and wherein the longevity measurement comprises at least a historical longevity parameter;

calculating, using the processor, a longevity parameter as a function of the longevity measurement and the health impact factor;

training, using the processor, a longevity machine learning model to generate a longevity classifier using a longevity training data, wherein the longevity training data contains a plurality of data entries correlating examples of longevity parameters to examples of longevity levels;

classifying, using the processor, the longevity parameter to a longevity level using the longevity classifier;

assigning, using the processor, the user the longevity level as a function of the classification, wherein the longevity level comprises a likelihood that a system of the user will make it to a given age without failure;

classifying the longevity parameter to the longevity level based on an if-then rule format, using an inference engine of a knowledge-based system (KBS);

updating the KBS based on previous longevity level classifications from the longevity machine learning model;

classifying an updated longevity parameter to an updated longevity level, using an updated inference engine of the KBS wherein a knowledge base of the KBS stores rules and longevity data in a subsumption ontology distinct from implicitly embedded procedural code and wherein the inference engine utilizes forward chaining to assert new facts from known facts and backward chaining to determine additional facts required to achieve a goal longevity level; and generating, using the processor, a longevity plan as a function of the updated longevity parameter and the updated longevity level, wherein generating the longevity plan comprises:

receiving first training data correlating input data, the input data including longevity levels, to longevity plan data;

training a neural network using the first training data, wherein the neural network is configured to output the longevity plan;

outputting the longevity plan to the user;

receiving user feedback regarding effects of the longevity plan;

receiving survey data related to a user's health after monitoring the longevity plan;

updating the longevity plan based on the user feedback and the survey data; and using the updated longevity plan as training data to train the neural network.

11. The method of claim 10, wherein the longevity parameter comprises an age comparison metric for the system of the user.

12. The method of claim 10, wherein the longevity parameter comprises a rate of aging.

13. The method of claim 10, wherein the longevity measurement comprises a biomarker associated with aging.

14. The method of claim 10, wherein the longevity level comprises a predicted life span of a given system.

15. The method of claim 10, wherein classifying the longevity parameter to the longevity level using the longevity classifier comprises assigning the longevity level as a function of a fuzzy inference.

16. The method of claim 10, wherein the longevity plan comprises a set of corrective measures configured to improve the user's longevity level.

17. The method of claim 10, wherein assigning the user the longevity level comprises assigning the longevity level as a function of a rate of aging.

18. The method of claim 10, wherein receiving the longevity measurement related to a user comprises receiving the longevity measurement from a longevity database.

\*   \*   \*   \*   \*